(12) United States Patent
Singer et al.

(10) Patent No.: US 6,849,120 B2
(45) Date of Patent: Feb. 1, 2005

(54) OXIDATION METHOD FOR PREPARING HIGHLY PURE MODAFINIL, CRYSTALLINE FORMS OF MODAFINIL, AND METHODS OF PREPARING THE CRYSTALLINE FORMS

(75) Inventors: Claude Singer, Kfar Saba (IL); Neomi Gershon, Kfar Saba (IL); Arina Ceausu, Rishon Lezion (IL); Anita Lieberman, Ramat Aviv (IL); Judith Aronhime, Rechovot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 106 days.

(21) Appl. No.: 09/916,885

(22) Filed: Jul. 27, 2001

(65) Prior Publication Data

US 2002/0043207 A1 Apr. 18, 2002

Related U.S. Application Data

(60) Provisional application No. 60/259,332, filed on Jan. 2, 2001, provisional application No. 60/230,088, filed on Sep. 5, 2000, provisional application No. 60/229,160, filed on Aug. 30, 2000, provisional application No. 60/226,491, filed on Aug. 18, 2000, and provisional application No. 60/221,110, filed on Jul. 27, 2000.

(51) Int. Cl.[7] .............................................. C30B 29/54
(52) U.S. Cl. ........................... 117/68; 117/69; 117/937; 117/939; 424/451; 424/464; 514/618
(58) Field of Search .............................. 117/68, 69, 939, 117/937; 514/618; 424/451, 464

(56) References Cited

U.S. PATENT DOCUMENTS

| 4,177,290 A | 12/1979 | Lafon |
| 4,927,855 A | 5/1990 | Lafon |
| 5,618,845 A | 4/1997 | Grebow et al. |
| 5,719,168 A | 2/1998 | Laurent |
| 6,348,500 B1 * | 2/2002 | Fu .............................. 514/618 |
| 6,465,519 B2 * | 10/2002 | Fu .............................. 514/618 |
| 2002/0183552 A1 * | 12/2002 | Naddaka et al. ............ 564/162 |

FOREIGN PATENT DOCUMENTS

| EP | 0 258 134 | 8/1987 |
| EP | 1260501 | * 11/2002 |

OTHER PUBLICATIONS

Josef Drabowicz et al. "A Convenient Procedure for the Oxidation of Sterically Hindered Sulfides to Sulfoxides" Synthesis—Journal of Synthetic Organic Chemistry—Oct. 1990.

Jerry March "Reactions, Mechanisms, and Structure" Advanced Organic Chemistry, Fourth Edition.

Th. Becue et al. "Confirmation of the Structure of by–products in the synthesis of Modafinil by liquid chromatography–mass spectrometry" Journal of Chromatography, 557 (1991) 489–494.

Renault J. Guillon et al "Synthesis and CNS Activity of New 3–Amino–3–arylpropionic Acid Derivatives", Pharm. Pharmacol. Commun. 1999, 5:217–223.

* cited by examiner

Primary Examiner—Robert Kunemund
(74) Attorney, Agent, or Firm—Kenyon & Kenyon

(57) ABSTRACT

The present invention provides an improved process for preparing modafinil, whereby it may be isolated in high purity by a single crystallization. The process produces modafinil free of sulphone products of over-oxidation and other byproducts. The invention further provides new crystalline Forms II–VI of modafinil and processes for preparing them. Each of the new forms is differentiated by a unique powder X-ray diffraction pattern. The invention further provides pharmaceutical compositions containing novel modafinil Forms II–IV and VI.

17 Claims, 6 Drawing Sheets

OXIDATION METHOD FOR PREPARING HIGHLY PURE MODAFINIL, CRYSTALLINE FORMS OF MODAFINIL, AND METHODS OF PREPARING THE CRYSTALLINE FORMS

CROSS-REFERENCE TO RELATED APPLICATIONS

The present application claims the benefit, under 35 U.S.C. § 119(e) of U.S. Provisional Applications Nos. 60/221,110, filed Jul. 27, 2000; 60/226,491, filed Aug. 18, 2000; 60/229,160, filed Aug. 30, 2000; 60/230,088 filed Sep. 5, 2000 and 60/259,332 filed Jan. 2, 2001 which are incorporated herein by reference.

FIELD OF THE INVENTION

The present invention relates to a process for preparing modafinil free of impurities, as well as new crystalline forms of modafinil and processes for their preparation.

BACKGROUND OF THE INVENTION (±)2-[(Diphenylmethyl)sulfinyl]acetamide of formula 1, also known as modafinil, exerts a wakefulness-promoting effect on humans and animals.

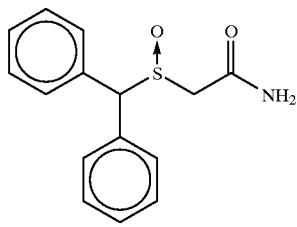

1

The psychotropic activity of modafinil was demonstrated in tests on animals such as those described in U.S. Pat. No. 4,177,290 ("the '290 patent") and in clinical trials on human patients. Modafinil racemate is approved by the F.D.A. for treatment of narcolepsy.

The '290 patent describes preparations of modafinil. In Example 1 of the '290 patent, modafinil is prepared by reacting 2-[(diphenylmethyl)thio]acetic acid chloride with ammonia, isolating the product amide and then oxidizing its sulfide group with hydrogen peroxide in acetic acid. Example 1a of the '290 patent describes a different synthetic method for an industrial scale preparation of modafinil. Benzhydrol is reacted with thiourea to form an intermediate which is then hydrolyzed to 2-[(diphenylmethyl)thio]acetic acid. The acid is then oxidized in situ with hydrogen peroxide in a mixture containing chloroacetic acid and water. The resulting sulfoxide is then treated with dimethyl sulfate to methylate the carboxylic acid group. The resulting ester is derivatized with ammonia to modafinil.

Each of these methods uses hydrogen peroxide to oxidize a sulfide group to a sulfoxide. Drabowicz, J et al. *Synthesis*, 1990, 37–38 describes a procedure for oxidizing sterically hindered sulfides to sulfoxides. The procedure uses hydrogen peroxide as the oxidizing agent, methanol as the solvent and a mixture of sulfuric acid and one of several branched aliphatic alcohols as a catalyst. The procedure is well adapted for oxidizing sterically hindered sulfides. No products of over-oxidation were observed by thin layer chromatography of the reaction mixtures. Use of this methodology to prepare modafinil has not been described in the literature.

Sulfides also may be oxidized to sulfoxides with other oxidizing agents, such as sodium periodate, t-butyl hypochlorite, calcium hypochlorite, sodium chlorite, sodium hypochlorite, meta-chloroperbenzoic acid and sodium perborate. March J. *Advanced Organic Chemistry* 1201–02 (4th ed. 1992).

We have discovered that the process of Example 1 of the '290 patent suffers from a problem of over-oxidation of the sulfide to sulphone 2.

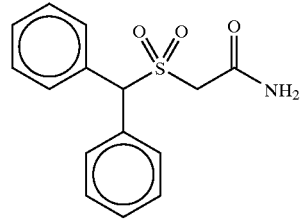

2

By comparing the above presented chemical structures it will be readily appreciated that separation of the sulphone once formed from modafinil is a difficult task. Therefore, the development of selective oxidation methods are required in order to obtain modafinil free of sulphone after one or more recrystallizations.

In the process described in Example 1a, significant amounts of intermediates 2-[(diphenylmethyl)sulfinyl]acetic acid 3 and methyl 2-[(diphenylmethyl)sulfinyl]acetate 4 are obtained because of incomplete conversion of the starting materials in Steps (b) and (c). Becue, T; Broquaire, M. *J Chromatography* 1991, 557, 489–494. These compounds are also difficult to separate from modafinil.

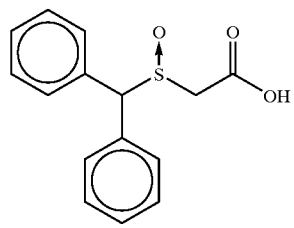

3

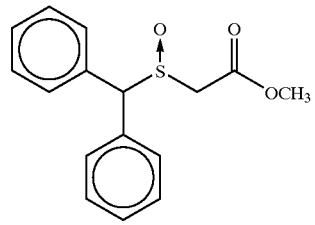

4

Due to the volume of solvent used by industrial scale processes and the environmental issues raised by the disposal of large amounts of organic solvent, an industrial preparation that yields modifinil essentially free of impurities and requires only one crystallization of the end product to obtain modifinil free of impurities within the limit of detection is highly advantageous over an alternative process that requires repeated recrystallizations to obtain modifil in equivalent purity. Although Example 1a of the '290 patent is described as an industrial process, two recrystallizations were used to obtain the product as a white crystalline powder. The composition of that powder is not reported.

It would be highly desirable to have an improved process that produces modafinil essentially free of sulphone 2 so that it may be obtained in high purity by a single crystallization. In addition, it also would be highly desirable to avoid using dimethyl sulfate, one of the reagents in Example 1a, since it is highly toxic.

While pursuing the object of efficiently producing modafinil in high purity, we discovered that modafinil can be crystallized into several distinct solid state crystalline polymorphic forms. Crystalline forms of a compound are differentiated by the positions of the atomic nuclei in the unit cell of the solidified compound. The differences produce different macroscopic properties like thermal behavior, vapor permeability and solubility, which have practical consequences in pharmacy. Crystalline forms of a compound are most readily distinguished by X-ray analysis. Single crystal X-ray crystalography yields data that can be used to determine the positions of the nuclei which in turn may be visualized with computer or mechanical models, thus providing a three-dimensional image of the compound. While single crystal X-ray studies provide unmatched structural information, they are expensive and quality data can sometimes be difficult to acquire. Powder X-ray diffraction spectroscopy is used more frequently by the pharmaceutical industry to characterize new crystalline forms of drugs than is single crystal X-ray analysis. Powder X-Ray diffraction spectroscopy yields a fingerprint that is unique to the crystalline form and is able distinguish it from the amorphous compound and all other crystalline forms of the compound.

There is a wide variety of techniques that have the potential of producing different crystalline forms of a compound. Examples include crystallization, crystal digestion, sublimation and thermal treatment. In the laboratory preparation in Example 1 of the '290 patent, modafinil is first precipitated by adding water to a reaction mixture containing modafinil, water and excess hydrogen peroxide. Modafinil is then recrystallized from methanol. In the industrial scale preparation of Example 1a, modafinil is obtained as a white powder by first crystallizing from a 1:4 mixture of methanol and water and then crystallizing again from a 1:9 methanol/water mixture. Crystallization from methanol and a 1:9 methanol/water mixture produces modafinil in polymorphic Form I. Modafinil Form I is characterized by a powder X-ray diffraction ("PXRD") pattern (FIG. 1) with reflections at 9.0, 10.2, 11.2, 12.9, 15.2, 15.8, 16.3, 17.7, 18.2, 19.3, 20.5, 21.6, 21.9, 23.2, 26.6±0.2 degrees 2θ.

U.S. Pat. No. 4,927,855 describes the preparation of the levorotatory enantiomer of modafinil by chiral resolution of the 2-[(diphenylmethyl)sulfinyl]acetic acid with α-methylbenzyl amine. After recovery and amidation of the enantiomerically pure acid, (−) modafinil was obtained as white crystals by crystallization from ethanol.

The discovery of a new crystalline form of a pharmaceutically useful compound provides an opportunity to improve the performance characteristics of a pharmaceutical product. It enlarges the repertoire of materials that a formulation scientist has available for designing, for example, a pharmaceutical dosage form of a drug with a targeted release profile or other desired characteristic. It is clearly advantageous when this repertoire is enlarged by the discovery of new crystalline forms of a useful compound. Five new crystalline forms of modafinil that are not accessible by following crystallization procedures previously described in the art have now been discovered.

SUMMARY OF THE INVENTION

Figure 1:
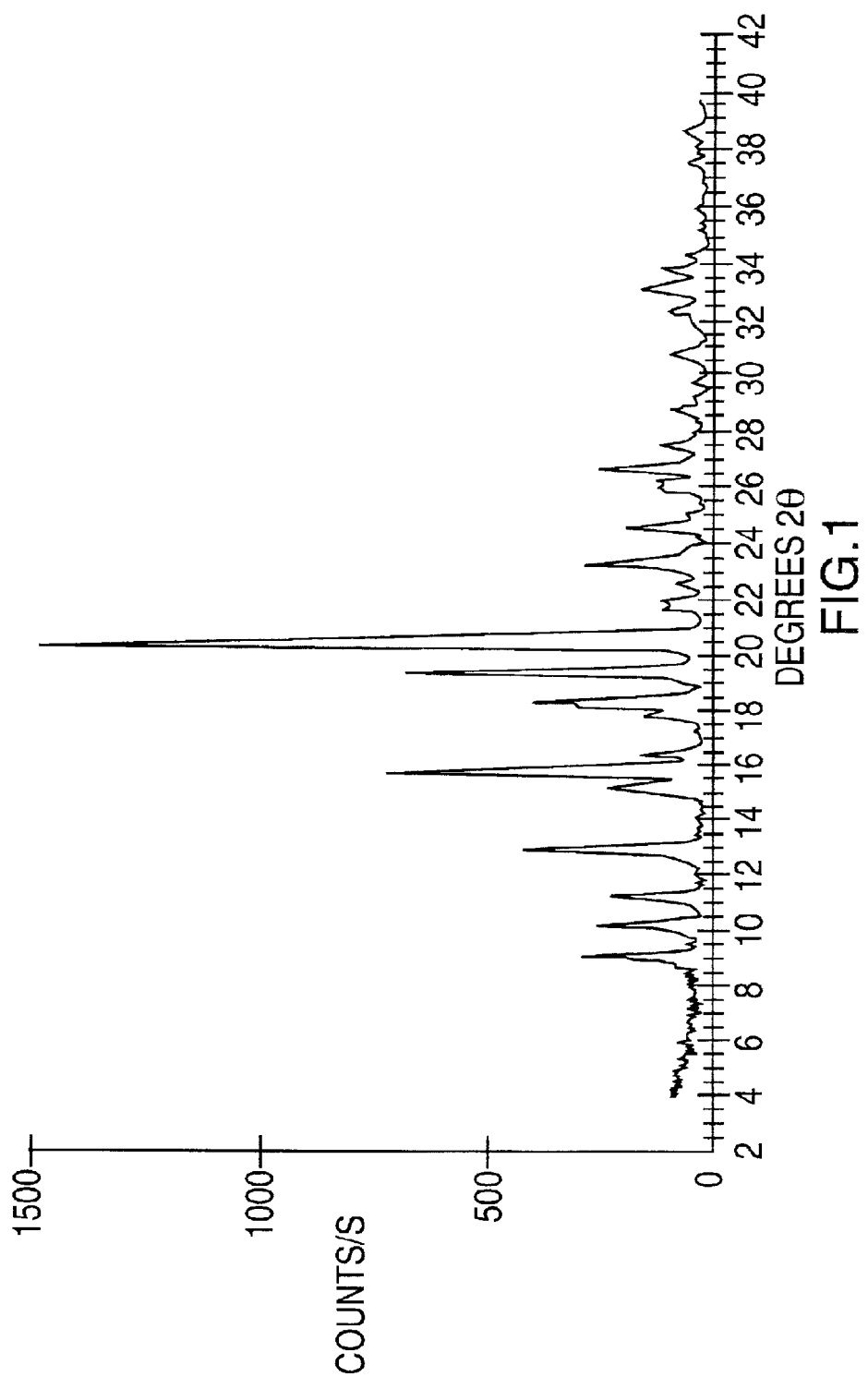
FIG. 1 represents an powder X-ray diffraction pattern of Modafinil Form I.

The present invention provides a process for preparing modafinil, whereby it may be isolated in high purity by a single crystallization. The process includes oxidation of 2-[(diphenylmethyl)thio]acetamide with $H_2O_2$ in a mixture of a mineral acid, an alcohol or phase transfer catalyst and optionally an inert liquid organic medium. Modafinil is precipitated from the reaction mixture and then crystallized in ≧99.5% purity. The oxidation method produces modafinil essentially free of sulphone products of over-oxidation which enables modafinil to be obtained free of sulphone within the limits of UV detection after two crystallizations.

The present invention further provides new crystalline Forms II–VI of modafinil and processes for preparing them. Each of the new forms is differentiated by a unique powder X-ray diffraction pattern.

The present invention further provides pharmaceutical compositions containing novel modafinil Forms II–IV and VI.

DETAILED DESCRIPTION OF THE PREFERRED EMBODIMENTS

In this disclosure, modafinil with a combined impurity content of less than 0.1% is referred to as "highly pure" modafinil. Purity is measured by UV absorbance at λ=225 nm. Compounds containing phenyl rings absorb strongly in this region of the U.V. spectrum. Modafinil and problematic impurities 2–4 each possess two phenyl UV chromophores. Modafinil that contains less than 0.01% of an impurity such as sulphone 2 is referred to as "essentially free" of that impurity and modafinil that is free of an impurity within the limit of detection of the purity analysis or that contains less than 0.0001% of the impurity is referred to as being "free" of that impurity.

The present invention provides an improved synthetic preparation of modafinil whereby modafinil may be isolated in ≧99.5% purity after a single recrystallization, preferably ≧99.9% purity. In this improved process, 2-[(diphenylmethyl)thio]acetamide is oxidized to modafinil. The modafinil is then separated as a solid from the reagents used in the oxidation and thereafter is isolated in high purity by a single recrystallization.

In the oxidation step, hydrogen peroxide is reacted with 2-[(diphenylmethyl)thio]acetamide in the presence of a mineral acid and a linear, branched or cyclic alcohol, or a phase transfer catalyst, optionally in an inert liquid organic medium. The oxidizing conditions are discussed generally in Drabowicz, J et al. *Synthesis*, 1990, 37–38. U.S. Pat. No. 4,177,290 is incorporated by reference for its teaching of a preparation of 2-[(diphenylmethyl)thio] acetamide.

Hydrogen peroxide is preferably supplied as a 10–50 wt. % solution in water, more preferably about 30–33 wt. % solution in water. Such solutions are commercially available (e.g. 1998–99 Aldrich Chemical Co. Cat. Nos. 42,065-4; 42,066-2; 31,698-9; 21,676-3).

Exemplary mineral acids that may be used include H₂SO₄, HClO₄ and H₃PO₄.

Preferred alcohols are derived from hydrocarbons with seven or fewer carbon atoms and that are unsubstituted except for the hydroxyl group. Branched alcohols are most preferred. Isopropyl alcohol, tert-butanol and 2-methyl-1-butanol are exemplary of alcohols that may be used. Suitable phase transfer catalysts include triethylbenzylammonium chloride (TEBA) and polyethylene glycol.

An inert liquid organic medium is a diluent for the oxidation reaction that may decrease the rate of the oxidation but does not prevent oxidation of the sulfide group of 2-[(diphenylmethyl)thio]acetamide to a sulfoxide group or cause overoxidation of the sulfide group to a sulphone. Preferred inert liquid organic media are unbranched alcohols such as methanol, ethanol and ethylene glycol; ketones, such as acetone, which may contain water; esters, such as ethyl acetate and dimethylcarbonate; and mixtures thereof.

In the oxidation step, 2-[(diphenylmethyl)thio]acetamide ("the sulfide") is contacted with an excess of hydrogen peroxide, preferably from about 1.5 to about 4 molar equivalents. The mineral acid need only be used in a catalytic amount, preferably from about 0.02 to about 0.2 molar equivalents with respect to the sulfide. The alcohol or phase transfer catalyst is preferably used in an amount of from about 2 to about 4 equivalents with respect to the sulfide, more preferably about 3 equivalents. When an inert liquid organic medium is used, the oxidation reaction is preferably conducted at a sulfide concentration of from about 0.07 to about 0.2 grams of sulfide per milliliter of inert liquid organic medium.

The required reagents may be added in any order desired and the reaction mixture may be maintained at any condition that causes oxidation of 2-[(diphenylmethyl) thio]acetamide to modafinil. The following procedure has been found in practice to produce modafinil in a sufficiently high state of purity directly by precipitation from the reaction mixture that modafinil may be therafter obtained in ≧99.5% purity, more preferrably greater than 99.9% purity, by a single crystallization. 2-[(Diphenylmethyl)thio]acetamide is suspended in the inert liquid organic medium. The mineral acid and the alcohol or phase transfer catalyst are then added at room temperature. Hydrogen peroxide is then added. The temperature of the reaction mixture is raised to about 30° C. and stirred for several hours. Progress of the reaction may be monitored by HPLC. After oxidation is complete, the reaction mixture is cooled to room temperature and the excess hydrogen peroxide is decomposed with, for example, sodium metabisulfite, sodium thiosulfide, sodium sulfide or ferrous sulfate.

After the oxidation is complete and any excess H₂O₂ has been decomposed, modafinil is precipitated from the reaction mixture. Precipitation can be accelerated by adding water. Modafinil is then separated from the reaction mixture by conventional means such as filtering or decanting. The modafinil preferably is then washed with an organic solvent and water.

The improved process for preparing modafinil produces modafinil with a low content of 2-[(diphenylmethyl) sulfonyl]acetamide 2,2-[(diphenyl methyl)sulphinyl]acetic acid 3, and methyl 2-[(diphenylmethyl)sulphinyl]acetate 4, which can be removed with a single recrystallization. The modafinil that precipitates from the reaction mixture should be 98–99% pure or greater and will typically contain less than 0. 1% suphone 2. Modafinil has been precipitated directly from the reaction mixture with less than 0. 01% contamination with sulphone 2. The composition of the oxidation reaction mixture may be monitored quantitatively by HPLC to confirm that the reaction is proceeding cleanly. A reverse phase HPLC method with UV detection at λ=225 nm may be used.

Although modafinil obtained by oxidation according to the above-described process may be recrystallized from a variety of solvents in high purity, the best recrystallization solvents have been found to be methanol, ethanol, dimethylcarbonate, acetone, and mixtures thereof. The best multicomponent solvent systems are ethanol/dimethylcarbonate, acetone/dimethylcarbonate, acetone/water, acetone/ethyl acetate, acetone/dimethylcarbonate/water and methanol/dimethylcarbonate. An especially preferred recrystallization solvent is dimethyl carbonate.

The modafinil that is obtained after crystallization is ≧99.5% pure, more preferably ≧99.9% pure and contains less than 0.02%, more preferably less than 0.01% of of sulphone 2. After crystallization from preferred recrystallization solvents, modafinil may be obtained free of sulphone 2, i.e. with no more than 0.0002% or 0.0001% contamination. It will be appreciated that such minute quantities of impurity are at or beyond the limits of detection of many analytical techniques.

In a second aspect, the present invention provides novel crystalline modafinil Forms II–VI and processes for their preparation.

A general technique that leads to the discovery of a novel crystalline form of a compound may be well known to those skilled in the art. In fact, that is commonly the case. Such techniques include crystallization, crystal digestion, sublimation, thermal treatment, and pH adjustment. Those skilled in the art will appreciate that in the search for new polymorphic forms of a compound, any one of these techniques is expected to fail to produce a new crystalline form of the compound. The search is an empirical exercise that involves trial and error experimentation with different techniques and conditions. For these reasons, it is not possible to define all techniques and conditions that will produce modafinil crystalline Forms II–VI. It is, however, possible to provide methods which have successfully and selectively produced modafinil in one of these desired forms.

The novel crystalline forms of modafinil have been characterized by powder X-ray diffraction spectroscopy which produces a fingerprint of the particular crystalline form. Measurements of 2θ values typically are accurate to within ±0.2 degrees.

X-ray diffraction data were acquired using a Philips powder X-ray diffractometer, Goniometer model 1050/70 at a scanning speed of 2° per minute, with a $Cu_{K\alpha}$ radiation of λ=1.5418 Å. The sample was gently ground and dusted over a zero background quartz plate to give a thin layer.

Modafinil Form I

The present invention provides processes for preparing modafinil Form I.

Modafinil Form I may prepared by crystallization from acetone, acetonitrile, benzyl alcohol, dimethyl formamide, methanol, methyl ethyl ketone or 2-pyrrolidone. Preferred recrystallization solvents are methanol and acetone. Crystallization may be accelerated by cooling the solution, adding an antisolvent or seeding the solution with a crystal of modafinil Form I. Preferred solvent/anti-solvent combinations are acetone/water, DMF/water, acetonitrile/water, ethanol/water and methanol/ethyl acetate.

Modafinil Form I also may be prepared by suspending a mixture of modafinil Forms I and II in ethyl acetate for a sufficient time to complete the conversion. If the starting modafinil form is Form II, then several other organic liquids may be substituted for ethyl acetate to promote conversion to Form I. In particular, Form II modafinil also may be converted into Form I modafinil by suspending it in methyl tert-butyl ether ("MTBE"), water or isobutyl acetate. It is particularly convenient to practice this technique for preparing Form I by simply slurrying modafinil (in any other form) with ethyl acetate, isobutyl acetate or water until the conversion is complete.

Forms V and VI convert into modafinil Form I upon gentle heating to about 80° C. or above. Forms V and VI may be transformed into Form I without significant decomposition by heating to about 100° C.

Modafinil Form I may be separated from solvents conventionally by filtering or decanting and then drying. Form I has been dried at a temperature as high as 100° C. without converting to another crystalline or amorphous form and without undergoing significant chemical decomposition.

Modafinil Form II

Figure 2:
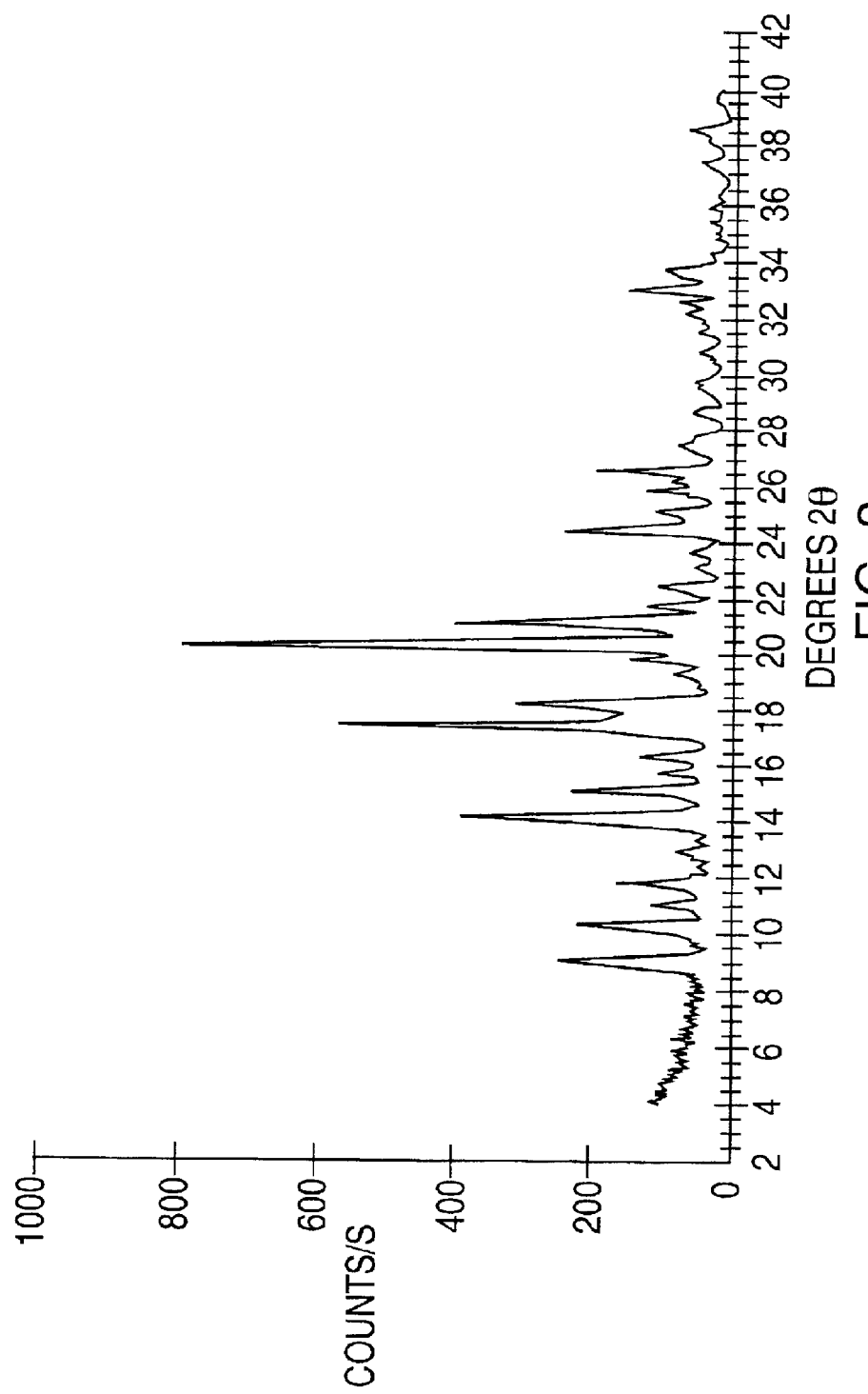
FIG. 2 represents an powder X-ray diffraction pattern of Modafinil Form II.

The present invention also provides modafinil Form II. Modafinil Form II produces a powder X-ray diffraction pattern (FIG. 2) with reflections at 9.1, 10.3, 11.1, 11.9, 14.3, 15.2, 16.4, 17.5, 18.4, 20.5, 21.3, 24.6, 26.6±0.2 degrees 2θ. The strong reflections at 14.3, 17.5, 20.5 and 21.3 degrees 2θ are particularly characteristic. Of these, the reflections at 14.3, 17.5 and 21.3 degrees 2θ are most characteristic.

The following techniques have proven effective for producing modafinil in crystalline Form II.

Modafinil Form III converts into modafinil Form II when it is suspended in water. Thus, suspending Form III in water provides a method of accessing modafinil Form II.

Modafinil also crystallizes selectively in Form II from ethanol, isopropanol, n-butanol, t-butanol, methyl isobutyl ketone, ethylene glycol, dioxolane and dioxane by heating to dissolve modafinil in the solvent and cooling to recrystallize. Modafinil Form II also may be prepared by reslurrying in dichloroethane and by rapidly cooling a solution of modafinil in a methanol and water mixture.

Modafinil Form III

Figure 3:
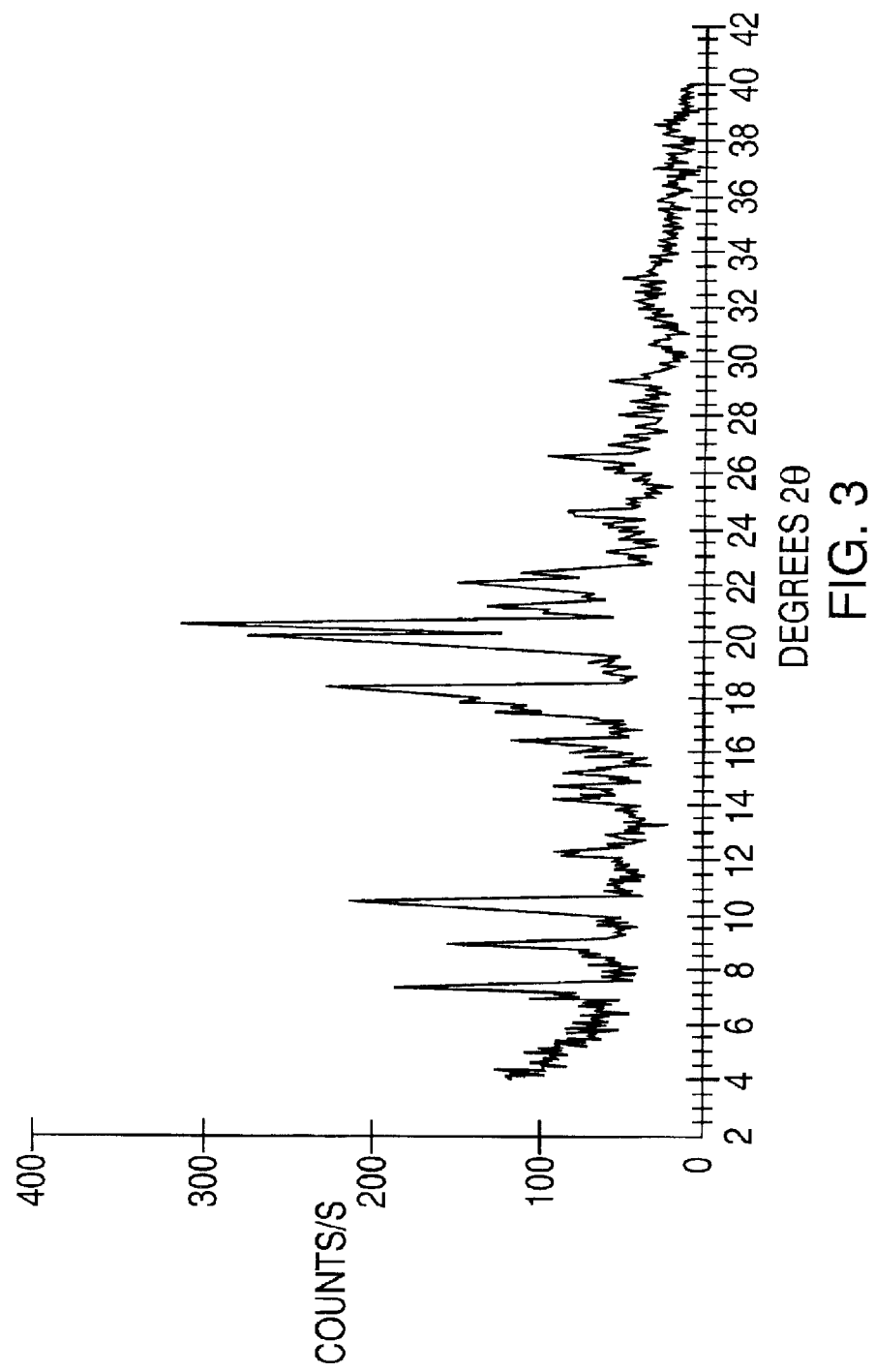
FIG. 3 represents an powder X-ray diffraction pattern of Modafinil Form III.

The present invention also provides modafinil Form III. Modafinil Form III produces a powder X-ray diffraction pattern (FIG. 3) with reflections at 7.4, 9.0, 10.5, 12.3, 14.2, 14.7, 15.1, 16.4, 18.3, 20.0, 20.5, 21.1, 22.1, 24.5±0.2 degrees 2θ. The strong reflections at 7.4, 10.5, 18.3, 20.0 and 20.5 degrees 2θ are particularly characteristic. Of these, the reflections at 7.4, 10.5, 18.3 and 20.0 degrees 2θ are characteristic for their intensity and the absence of reflections at corresponding positions in the PXRD patterns of the other forms.

Modafinil Form III is produced by crystallization from toluene. Form III has also been crystallized from mixtures of dimethyl carbonate and ethanol, although it has in instances been obtained in mixture with Form V when crystallized from this mixed solvent system.

Modafinil Form IV

Figure 4:
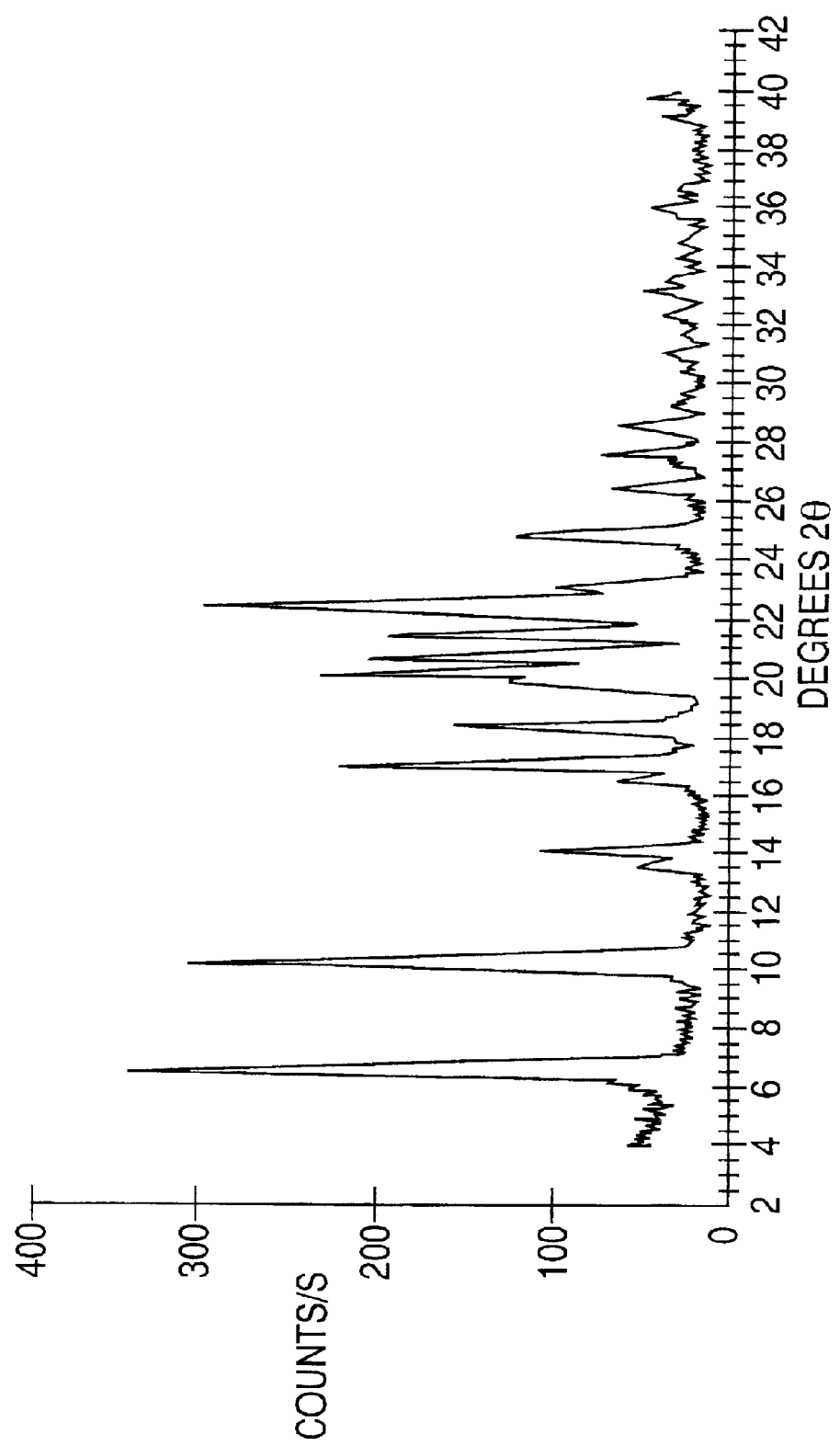
FIG. 4 represents an powder X-ray diffraction pattern of Modafinil Form IV.

The present invention also provides modafinil Form IV. Modafinil Form IV produces a powder X-ray diffraction pattern (FIG. 4) with reflections at 6.9, 10.4, 14.1, 17.2, 18.5, 20.3, 20.8, 21.6, 22.7, 25.0, 26.5, 27.6, 28.5±0.2 degrees 2θ. The strong reflections at 6.9, 10.4, 17.2, 20.3 and 22.7 degrees 2θ are particularly characteristic.

Modafinil crystallizes from tetrahydrofuran and dimethyl sulfoxide in crystalline Form IV.

Modafinil Form V

Figure 5:
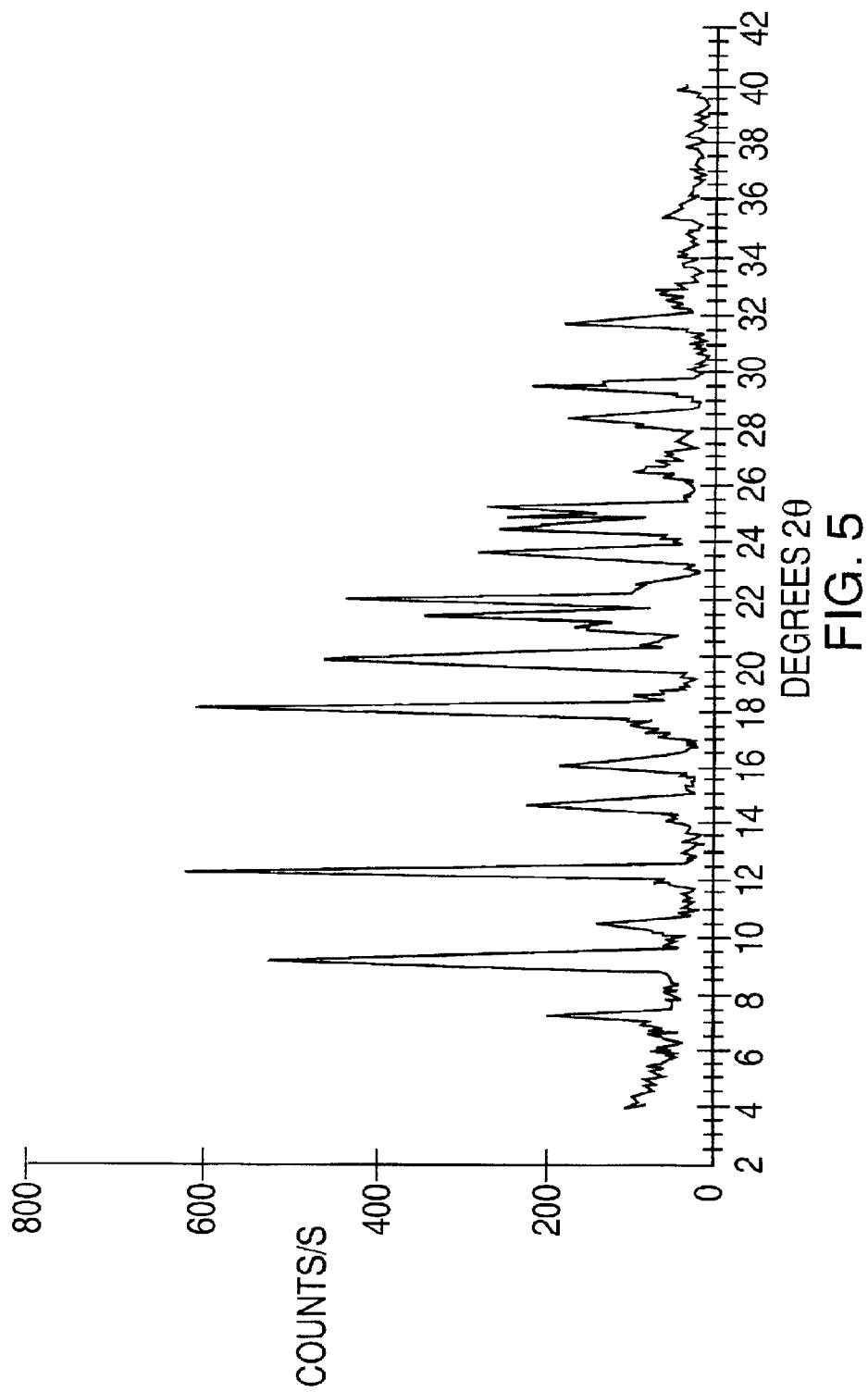
FIG. 5 represents an powder X-ray diffraction pattern of Modafinil Form V.

The present invention also provides modafinil Form V. Form V produces a powder X-ray diffraction pattern (FIG. 5) with reflections at 7.4, 9.3, 10.5, 12.4, 14.7, 16.2, 18.2, 19.9, 21.5, 22.0, 23.6, 24.5, 25.2, 28.4, 29.5, 31.8±0.2 degrees 2θ. The strong reflections at 9.3, 12.4, 18.2, 19.9, and 22.0 degrees 2θ are particularly characteristic.

Form V is prepared by crystallization from dimethylcarbonate and mixtures of dimethylcarbonate and ethanol, dimethylcarbonate and water and dimethylcarbonate and acetone.

Thermogravimetric analysis of Form V showed a mass loss of about 12% starting at about 100° C. up to 150° C. This LOD is consistent with Form V being a hemi-solvate of modafinil with dimethylcarbonate. The TGA analysis was performed on a Shimadzu DTG 60, with a sample of about 10 mg that was heated at the rate of about 10° C. per min from about ambient temperature to about 300° C.

Modafinil Form VI

Figure 6:
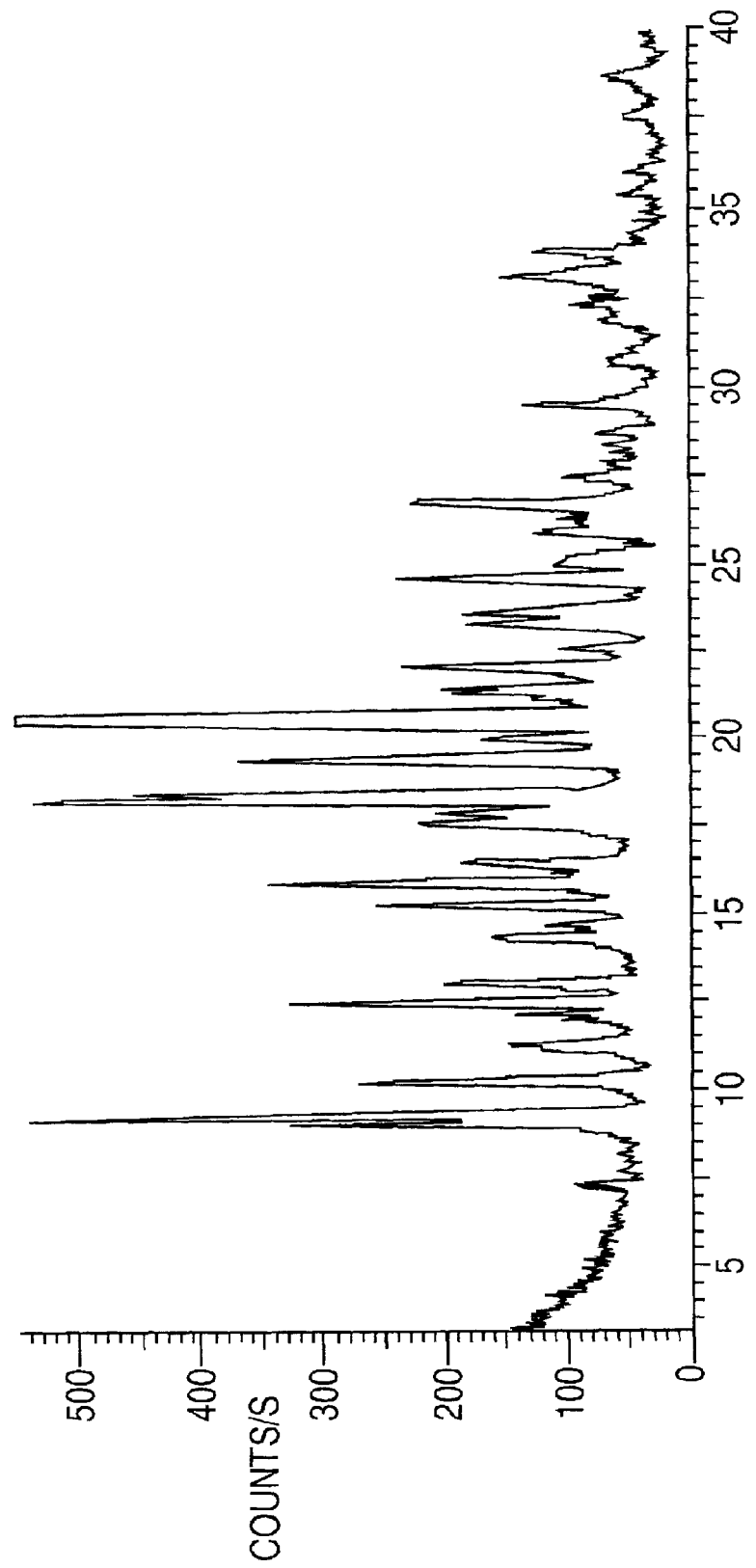
FIG. 6 represents an powder X-ray diffraction pattern of Modafinil Form VI.

The present invention also provides modafinil Form VI. Form VI produces a powder X-ray diffraction pattern (FIG. 6) with reflections at 9.0, 9.3, 10.2, 12.4, 14.2, 14.5, 15.3, 17.5, 18.1, 20.0, 20.5, 21.5, 22.0, 23.5, 24.5, 25.0±0.2 degrees 2θ. The reflections at 9.3, 18.1, and 20.5 degrees 2θ are particularly characteristic for their intensity.

Modafinil Form VI may be prepared by suspending modafinil Form V in water, ethanol or a water/ethanol mixture for a sufficient time to complete the conversion. Preferably, modafinil Form VI is slurried in water, ethanol, or an ethanol/water mixture at about 28° C., followed by drying under vacuum at 55° C.

Amorphous Modafinil

Modafinil may be prepared in an amorphous state by crystallization from mixtures of ortho, meta or para xylene.

Having described techniques best suited for producing distinct crystalline Forms II–VI of modafinil in a laboratory and industrial setting, those skilled in the art will appreciate that these forms may be accessible by yet other methods.

Pharmaceutical Compositions Containing Modafinil Forms II–IV and VI

Modafinil Forms II–IV and VI may be formulated into a variety of pharmaceutical compositions and dosage forms that are useful for promoting wakefulness in patients afflicted with narcopolepsy.

Pharmaceutical compositions of the present invention contain modafinil Forms II–IV and VI, optionally in mixture with each other. Pharmaceutical compositions of the present invention also may contain other modafinil crystalline forms, amorphous modafinil and/or other active ingredients in mixture with one or more of modafinil Forms II–IV and VI. In addition to the active ingredient(s), modafinil pharmaceutical compositions of the present invention may contain one or more excipients. Excipients are added to the composition for a variety of purposes.

Diluents increase the bulk of a solid pharmaceutical composition and may make a pharmaceutical dosage form containing the composition easier for the patient and caregiver to handle. Diluents for solid compositions include, for example, microcrystalline cellulose (e. g. Avicel®), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flow properties of non-compacted solid compositions and improve the accuracy of dosing. Excipients that may function as glidants include colloidal silicon dixoide, magnesium trisilicate, powdered cellulose, starch, talc and tribasic calcium phosphate.

When a dosage form such as a tablet is made by compaction of a powdered composition, the composition is subjected to pressure from a punch and dye. Some excipients and active ingredients have a tendancy to adhere to the surfaces of the punch and dye, which can cause the product to have pitting and other surface irregularities. A lubricant can be added to the composition to reduce adhesion and ease release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid ethyl maltol, and tartaric acid.

Compositions may also be colored using any pharmaceutically acceptable colorant to improve their appearance and/or facilitate patient identification of the product and unit dosage level.

Selection of excipients and the amounts to use may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges as well as liquid syrups, suspensions and elixirs. An especially preferred dosage form of the present invention is a tablet.

Tablets, capsules, lozenges and other unit dosage forms preferably contain modafinil in a dosage level of from about 50 to about 300 mg, more preferably from about 100 mg to about 200 mg.

Having described the invention with reference to certain preferred embodiments, the following examples are provided for the purpose of illustrating, but not limiting, the invention.

EXAMPLES

Examples 1–8
(Preparations of Highly Pure Modafinil)

Example 1

In a three necked round bottom flask equipped with reflux condenser, a thermometer and an agitator, diphenylmethylthio-2-acetamide (50 g) was suspended in methanol (550 ml). A solution (44 ml) containing 1.2 ml $H_2SO_4$ dissolved in 46.7 ml isopropanol was added. A 30% solution of $H_2O_2$ (45 ml) was added, causing the temperature to rise to 30° C. The temperature was maintained at 30° C. for 3.5 h. The reaction mass was cooled to 25° C. and diluted with 450 ml of water. The excess of unreacted $H_2O_2$ was neutralized with $Na_2S_2O_5$ and additional 50 ml of water was added. modafinil was separated by filtration and reslurried with 210 ml water. After drying 40.2 g modafinil was obtained (yield: 75.7%).

Example 2

In a three necked round bottom flask equipped with a reflux condenser, a thermometer and an agitator, diphenylmethylthio-2-acetamide (50 g) was suspended in dimethylcarbonate (550 ml). A solution (44 ml) containing 1.2 ml $H_2SO_4$ dissolved in 46.7 ml isopropanol was added. A 15% solution of $H_2O_2$ (85 ml) was added, causing the temperature to rise to 30° C. The temperature was maintained at 30° C. for 30 h. The reaction mass was cooled to 25° C. and diluted with 450 ml of water. The excess of unreacted $H_2O_2$ was neutralized with $Na_2S_2O_5$ and additional 50 ml of water was added. modafinil was separated by filtration and reslurried with 210 ml water. After drying 45.1 g modafinil was obtained (yield 85%).

Example 3

In a three necked round bottom flask equipped with reflux condenser, a thermometer, and an agitator, 3 g of modafinil prepared as in Example 1 was suspended in 32 ml acetone containing 5% water. The mixture was heated to reflux (~58° C.) under a nitrogen atmosphere. The solution so obtained was cooled to 42° C. at which temperature crystallization starts. The suspension was further cooled to 25° C. and filtered. After drying, 1.95 g of highly purified modafinil essentially free of sulphone was obtained (yield: 65%).

Example 4

In a three necked round bottom flask equipped with reflux condenser, a thermometer, and an agitator, 1 g of modafinil prepared as in Example 2 was suspended in 10.5 ml ethanol. The mixture was heated to reflux under nitrogen. The suspension was cooled to 25 ° C. and filtered. After drying 0.83 g of highly purified modafinil was obtained (yield: 83%).

Example 5

In a three necked round bottom flask equipped with reflux condenser, a thermometer and an agitator, diphenylmethylthio-2-acetamide (50 g) was suspended in dimethylcarbonate (550 ml). A solution (44 ml) containing 1.2 ml $H_2SO_4$ dissolved in 46.7 ml isopropanol was added. Further 49 ml of 30% $H_2O_2$ was added. The temperature increases to 30° C. and was maintained constant during 8 h. The reaction mass was cooled to 25° C. and diluted with 450 ml of water. The excess of unreacted $H_2O_2$ was neutralized with $Na_2S_2O_5$ and additional 50 ml of water was added. Modafinil was separated by filtration and reslurried with 210 ml water. After drying 45.1 g modafinil was obtained (yield 85%).

Example 6

In a three necked round bottom flask equipped with reflux condenser, a thermometer, and an agitator, 3 g of modafinil prepared as in Example 5 was suspended in a mixture containing 100 ml acetone and 20 ml dimethylcarbonate. Under nitrogen, the mixture was heated to reflux (~58° C.). The solution so obtained was cooled to 47° C. at which temperature crystallization starts. The suspension was further cooled to 25° C. and filtered. After drying 2.52 g of highly purified modafinil essentially free of sulphone was obtained (yield: 84%).

Example 7

In a three necked round bottom flask equipped with reflux condenser, a thermometer, and an agitator, 3.7 g of undried modafinil obtained in Example 6 was suspended in a mixture containing 123.5 ml acetone and 24.7 ml dimethylcarbonate. Under nitrogen the mixture was heated to reflux (~58° C.). The obtained solution was cooled to 25° C. and filtered. The filter cake was dried and again suspended in a mixture of 94.5 ml acetone and 19 ml dimethylcarbonate and under nitrogen heated to reflux. The solution so obtained was cooled to 25° C. and filtered. After drying 2.32 g of highly purified modafinil free of sulphone was obtained (yield: 62.7%).

Example 8

In a three necked round bottom flask equipped with reflux condenser, a thermometer, and an agitator, 3 g of modafinil prepared as in Example 5 was suspended in a mixture containing 1 ml acetone and 20 ml dimethylcarbonate. Under nitrogen, the mixture was heated to reflux (~58° C.). The obtained solution was cooled to 25° C. and filtered. The wet filter cake was again suspended in a mixture of 100 ml acetone and 20 ml dimethylcarbonate and under nitrogen heated to reflux. The solution so obtained was cooled to 25° C. and filtered. After drying, 2.1 g of highly purified modafinil free of sulphone was obtained (yield: 70.5%).

Examples 9–13
(Preparations of Modafinil Form I)

Example 9
By Suspending Modafinil Form IV in Water.

Modafinil Form IV (0.4 g) was suspended in distilled water (50 ml) with a pH of about 5.9. The suspension was stirred for about 24 hours at about 37° C. and then filtered. The filtrate was analyzed by x-ray powder diffraction and was determined to be modafinil Form I.

Example 10
By Heating Modafinil Forms V or VI

A small aliquot of Modafinil Forms V and VI are heated separately, for about 30 minutes, in an oven at about 100° C. Modafinil Forms V and VI were subsequently analyzed by x-ray powder diffraction and both were determined to be Form I.

Example 11
Crystallization from Acetonitrile.

Modafinil (3 g) was suspended in acetonitrile (23 ml) in a three-necked round bottom flask equipped with a reflux condenser, a thermometer, and an agitator. The mixture was heated to reflux (about 80° C.). The resulting solution was cooled to about 63° C. at which point crystallization began. The suspension was furthered cooled to about 25° C. and then filtered. After drying, crystallized modafinil (1.96 g) Form I was obtained (65% yield).

Example 12
Crystallization from Dimethylformamide.

Modafinil (3 g) was suspended in dimethylformamide (5.5 ml) in a three-necked round bottom flask equipped with a reflux condenser, a thermometer, and an agitator. The mixture was heated to reflux (about 60° C.). A clear solution was obtained. Water (5 ml) was added dropwise to the solution which caused modafinil to begin precipitating. Precipitation was completed by cooling the mixture to about 25° C. The product was separated by filtration. After drying, crystallized modafinil (2.54 g) Form I was obtained (84.7% yield).

Example 13
Crystallization from Ethyl Acetate.

Modafinil (3 g) was suspended in ethyl acetate (50 ml) in a three-necked round bottom flask equipped with a reflux condenser, a thermometer, and an agitator,. The mixture was heated to reflux (about 77° C.) and maintained for about 1 hour. The mixture was cooled to about 25 C. and then was filtered. After drying, crystallized modafinil Form I (1.9 g) was obtained (63% yield).

Examples 14–15
(Preparation of Modafinil Form II)

Example 14
Crystallization from Isopropanol.

Modafinil (3 g) was suspended in isopropanol (34 ml) in a three-necked round bottom flask equipped with a reflux condenser, a thermometer, and an agitator. The mixture was heated to reflux (about 85° C.). The resulting solution was cooled to about 58° C. at which point crystallization began. The suspension was cooled to about 25° C. and then was filtered. After drying, crystallized modafinil Form II (2.32 g) was obtained (77.3% yield).

Example 15
From a Suspension of Modafinil Form III in Water:

Modafinil Form III (0.4 g) was suspended in distilled water (50 ml) having a pH of about 5.9. The suspension was stirred for about 24 hours at about 37° C. and then was filtered. The filtrate was analyzed by powder X-ray diffraction and was determined to be modafinal Form II.

Example 16
(Preparation of Modafinil Form III)

Example 16
Crystallization from Toluene.

Modafinil (3 g) was suspended in of toluene (90 ml) in a three-necked round bottom flask equipped with a reflux condenser, a thermometer, and an agitator. The mixture was heated to reflux (about 110°C.). The resulting solution was cooled to about 35° C. at which point crystallization began. The suspension was maintained for about 17 hours at about 25° C., cooled to about 5° C., and then was filtered. After drying, crystallized modafinil (0.6 g) Form III was obtained (19.6% yield).

Example 17
(Preparation of Modafinil Form IV)

Example 17
Crystallization from Tetrahydrofuran.

Modafinil (3 g) was suspended in tetrahydrofuran (90 ml) in a three-necked round bottom flask equipped with a reflux condenser, a thermometer, and an agitator. The mixture is heated to reflux (about 63° C.). The resulting solution was cooled to about 53° C. at which point crystallization began. The suspension was cooled to about 25° C. and then was filtered. After drying, crystallized (2.4 g) modafinil Form IV was obtained (80% yield).

Example 18
(Preparation of Modafinil Form V)

Example 18
Crystallization from Dimethylcarbonate.

Modafinil (3 g) was suspended in dimethylcarbonate (105 ml). The mixture was heated to reflux (about 90° C.) in a three-necked round bottom flask equipped with a reflux condenser, a thermometer, and an agitator. After about 2 hours at reflux, the resulting solution was cooled to about 79° C. at which point crystallization began. The suspension was cooled to about 25° C. and then was filtered. After drying, about crystallized modafinil (3 g) Form V was obtained (about 90% yield).

Example 19
(Preparation of Modafinil Form VI)

Example 19
From a Suspension of Form V in Ethanol.

Modafinil (3.5 g) Form V was suspended in ethanol (10 ml) in a three-necked round bottom flask equipped with a descending condenser, a thermometer, and an agitator. The mixture was stirred for about 4.5 hours at about 25° C. and then was filtered. After drying, crystallized modafinil (2.9 g) Form VI was obtained (82% yield).

Example 20
(Preparation of Amorphous Modafinil)

Example 20
Crystallization from Xylenes.

Modafinil (5 g) was suspended in of xylene (150 ml) in a three-necked round bottom flask equipped with a descending condenser, a thermometer and an agitator. The mixture was heated to about 110° C., which was maintained for about 30 minutes. The resulting solution was cooled to about 35° C. at which point crystallization began. The suspension was maintained for about 17 hours at about 25° C., then cooled to about 5° C., and then was filtered. After drying, amorphous modafinil (1.83 g) was obtained (36.6% yield).

Having thus described the invention with reference to certain preferred embodiments, other embodiments will become apparent to one skilled in the art from consideration of the specification and examples. It is intended that the specification, including the examples, is exemplary only, with the scope and spirit of the invention being defined by the claims which follow.

We claim:

1. A process for preparing modafinil comprising the steps of:

a) oxidizing 2-[(diphenylmethyl)thio]acetamide in a mixture comprising $H_2O_2$, a mineral acid, and either an alcohol or phase transfer catalyst, b) precipitating a solid containing modafinil from the mixture, and c) separating the mixture from the precipitated solid.

2. The process of claim 1 further comprising isolating modafinil in purity greater than or equal to 99.5% from the precipitated solid by a single crystallization.

3. The process of claim 2 wherein the modafinil is isolated in purity greater than or equal to 99.9% from the precipitated solid by a single crystallization.

4. The process of claim 1 wherein the modafinil is isolated in pharmaceutically acceptable purity.

5. The process of claim 1 wherein the purity of the modafinil is measured by the relative area of peaks in a chromatogram obtained by ultraviolet detection using 225 nm wavelength light.

6. The process of claim 1 wherein the precipitated solid is modafinil in greater than or equal to 99% purity.

7. The process of claim 6 wherein the precipitated solid is modafinil in greater than or equal to 99.5% purity.

8. The process of claim 1 wherein the $H_2O_2$ is added to the mixture as a 10–50 weight percent solution in water.

9. The process of claim 1 wherein the mineral acid is selected from the group consisting of sulfuric acid, perchloric acid, and phosphoric acid.

10. The process of claim 1 wherein the alcohol is selected from the group consisting of isopropanol, tert-butanol, and 2-methyl-1-butanol.

11. The process of claim 1 wherein the mixture further includes an inert liquid organic medium.

12. The process of claim 11 wherein the inert liquid organic medium is selected from the group consisting of methanol, ethanol, ethylene glycol, acetone, dimethylcarbonate, and mixtures thereof.

13. The process of claim 11 wherein the oxidizing comprises suspending one equivalent of the 2-[(diphenylmethyl)thio]acetamide in an inert liquid organic medium in an amount of 0.07 to about 0.13 grams per milliliter, adding from about 0.05 to about 0.2 molar equivalents of the mineral acid, from about 2 to about 4 equivalents of the alcohol and from about 1.5 to about 4 molar equivalents of $H_2O_2$ to the liquid organic medium.

14. The process of claim 13 wherein oxidizing further comprises heating the inert liquid organic medium.

15. The process of claim 1, wherein the mineral acid is present in a catalytic amount with respect to the 2-[(diphenylmethyl)thio]acetamide.

16. The process of claim 1, wherein the catalytic amount is from about 0.02 to about 0.2 molar equivalents of mineral acid.

17. The process of claim 2, wherein the single crystallization is a crystallization from acetone.

* * * * *

UNITED STATES PATENT AND TRADEMARK OFFICE
CERTIFICATE OF CORRECTION

PATENT NO. : 6,849,120 B2
DATED : February 1, 2005
INVENTOR(S) : Singer et al.

It is certified that error appears in the above-identified patent and that said Letters Patent is hereby corrected as shown below:

<u>Column 2,</u>
Lines 57 and 59, change "modifinil" to -- modafinil --.
Line 61, change "modifil" to -- modafinil --.

<u>Column 3,</u>
Line 15, change "crystalography" to -- crystallography --.

<u>Column 5,</u>
Line 39, change "therafter" to -- thereafter --.
Line 40, change "perferrably" to -- preferably --.

<u>Column 6,</u>
Line 18, change "of of" to -- of --.

<u>Column 8,</u>
Line 41, change "narcopolepsy" to -- narcolepsy --.
Line 57, change "pregelitinized" to -- pregelatinized --.

UNITED STATES PATENT AND TRADEMARK OFFICE
CERTIFICATE OF CORRECTION

PATENT NO. : 6,849,120 B2
DATED : February 1, 2005
INVENTOR(S) : Singer et al.

It is certified that error appears in the above-identified patent and that said Letters Patent is hereby corrected as shown below:

Column 9,
Lines 28, 30 and 32, change "dye" to -- die --.
Line 29, change "tendancy" to -- tendency --.
Line 64, change "losenges" to -- lozenges --.

Column 10,
Line 26, change "added. modafinil" to -- added. Modafinil --.

Column 12,
Line 33, change "agitator,." to -- agitator. --.
Line 58, change "modafinal" to -- modafinil --.

Signed and Sealed this

Thirtieth Day of August, 2005

JON W. DUDAS
*Director of the United States Patent and Trademark Office*